United States Patent [19]

Ingelman et al.

[11] 3,980,770

[45] Sept. 14, 1976

[54] POLYMERIZATION PRODUCTS CONTAINING AMINO GROUPS USEFUL IN SERUM CHOLESTEROL LEVEL CONTROL

[75] Inventors: Björn G.-A. Ingelman; Bernt J. Lindberg; Jan G. Rosengren, all of Uppsala; Dag E. S. Campbell, Sigtuna, all of Sweden

[73] Assignee: Pharmacia Aktiebolag, Uppsala, Sweden

[22] Filed: Dec. 5, 1974

[21] Appl. No.: 529,987

Related U.S. Application Data

[63] Continuation of Ser. No. 257,734, May 30, 1972, abandoned.

[30] Foreign Application Priority Data

June 4, 1971 Sweden.............................. 7219/71

[52] U.S. Cl................................... 424/79; 424/78; 424/330
[51] Int. Cl.² ..................... A61K 31/74; A01N 9/20; A01N 9/24
[58] Field of Search ................ 424/79, 330; 260/2.1

[56] References Cited
UNITED STATES PATENTS

| | | | |
|---|---|---|---|
| 2,106,486 | 1/1938 | Kirkpatrick | 260/2.1 R |
| 2,469,683 | 5/1949 | Dudley et al. | 260/2 |
| 2,582,849 | 1/1952 | Ramondt | 260/72.5 |
| 3,265,663 | 8/1966 | Lloyd | 260/47 |
| 3,383,281 | 5/1968 | Wolf et al. | 260/2.1 E |
| 3,627,872 | 12/1971 | Parkinson | 424/79 |

FOREIGN PATENTS OR APPLICATIONS

| | | |
|---|---|---|
| 634,985 | 1/1962 | Canada ........................... 260/2.1 C |
| 1,488,152 | 5/1967 | France |
| 1,900,124 | 1/1969 | Germany |
| 731,030 | 2/1943 | Germany |

OTHER PUBLICATIONS

Chem. Abst. 55 1073(c), (1961) "Curable Epoxy Resin Compositions", Bender et al.

Chem. Abst. 69, 35614(e) (1968) "Reaction of Propylene Epoxide w/p- and m-Xylylenediamines" - Zhubanov et al.

*Primary Examiner*—Sam Rosen
*Assistant Examiner*—D. W. Robinson
*Attorney, Agent, or Firm*—Fred Philpitt

[57] ABSTRACT

A pharmaceutical product containing amino groups, which product:

a. is comprised of residues of one or more diamines of the general formula

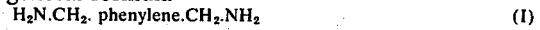
$$H_2N.CH_2.\text{phenylene}.CH_2.NH_2 \qquad (I)$$

which residues are interconnected by bridges between the residues to form a three-dimensional network, the bridges being bound to nitrogen atoms in the residues (I) and comprise straight or branched aliphatic, saturated hydrocarbon chains substituted with one or more hydroxyl groups and containing 3–30 carbon atoms, preferably 3–16 carbon atoms and which are optionally broken by one or more oxygen atoms, the amino groups being present in a free form or in the form of (the cation portion of) a non-toxic salt, and b. is insoluble in water or other solvents, but capable of swelling in water to gel form, 1 g of the dry product in the form of an HCl salt in the presence of water swelling to at least 5 ml and to at most 50 ml, preferably to at least 5 ml and to at most 25 ml, and c. is in grain form having a particle size substantially within the range of 1 to 1000 μ, preferably 10 to 800 μ, and d. has an ion-exchange capacity within the range of 0.2 to 1 milliequivalents chloride ions, preferably 0.3 to 0.9 milliequivalents chloride ions, per 100 mg of dry gel, a method for its preparation and use for lowering the cholesterol content of the blood of mammals and birds.

14 Claims, No Drawings

POLYMERIZATION PRODUCTS CONTAINING AMINO GROUPS USEFUL IN SERUM CHOLESTEROL LEVEL CONTROL

This is a continuation of application Ser. No. 257,734, filed May 30, 1972, now abandoned.

The present invention relates to polymerization products containing amino groups and a method of producing such products. The products are intended to be used as ion-exchangers for therapeutical purposes, as cholesterol reducing agents, in which case when taken orally the ion-exchanger acts as a binding agent for bile acids in the intestines.

A number of known polymerization products containing amino groups are utilized as ion-exchangers for the aforementioned purpose. One type of such a polymer can be produced by copolymerizing a polyamine with a cross-linking agent to form a product which can be administered orally in granular form.

The present invention now provides a polymerization product containing amino groups which possesses extremely advantageous properties in a number of important respects.

The polymerization product containing amino groups in accordance with the invention is suitable for use as an ion-exchanger for therapeutical purposes and is characterized by the fact that it a. comprises residues of one or more diamines of the general formula $$H_2N.CH_2.phenylene.CH_2.NH_2 \quad (I)$$

which residues are interconnected by bridges between the residues to form a three-dimensional network, the bridges being bound to nitrogen atoms in the residues (I) and comprise straight or branched aliphatic, saturated hydrocarbon chains substituted with one or more hydroxyl groups and containing 3–30 carbon atoms, preferably 3–16 carbon atoms and which are optionally broken by one or more oxygen atoms, the amino groups being present in a free form or in the form of (the cation portion of) a non-toxic salt, and b. is insoluble in water or other solvents but capable of swelling in water to gel from, 1 gr of the dry product in the form of an HCl salt in the presence of water swelling to at least 5 ml and to at most 50 ml, preferably to at least 5 ml and to at most 25 ml, and c. is in grain form having a particle size substantially within the range of 1 to 1000 μ, preferably 10 to 800 μ, and d. has an ion-exchange capacity within the range of 0.2 to 1 milliequivalent chloride ions, preferably 0.3 to 0.9 milliequivalent chloride ions, per 100 mg of dry gel.

In accordance with the invention, the extent to which the polymerization product swells in water is measured as required, by transferring $y$ grams of the granular product in dry form to a measuring glass. Water is then poured into the glass in a quantity such that when swelling of the polymerization product is completed the water still covers the swollen product. The volume occupied by the swollen product is read off, and the obtained value in ml is divided by $y$ to establish the amount to which 1 gram of the dry product will swell in the presence of water.

As previously mentioned, 1 gram of the dry product in the form of an HCl salt shall sell in water to at least 5 ml and to at most 50 ml. Normally, the product swells to between 5 and 30 ml, preferably to between 5 and 25 ml, the range of 8 to 20 ml being mentioned as an example.

The aminomethyl groups may occupy any position in the diamine of formula I. Preferably, the groups are located in m- or p-position. The diamine used is normally a mixture of diamines with the aminomethyl groups in m- and p-position. Such products are commersially available.

By residues of diamines of the formula I is meant here and in the claims residues of the formula

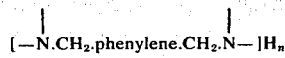

where $n$ is an integer lower than 4.

Cross-linking of the residues of the diamines (I) is thus effected by substituting hydrogen atoms on the nitrogen atoms in the diamine molecules with residues —R— from the cross-linking agent. The nitrogen atoms may also be quaternized by means of the bridges or by salt formation.

As examples of the residue —R— can be mentioned:
—$CH_2.CH(OH).CH_2$— or

—$CH_2.CH(OH).CH_2.O.CH_2.CH(OH).CH_2$— or

—$CH_2.CH(OH).CH_2.O.CH_2.CH_2.O.CH_2.CH(OH).CH_2$— or

—$CH_2.CH(OH).CH_2.O.(CH_2)_4.O.CH_2.CH(OH).CH_2$— or

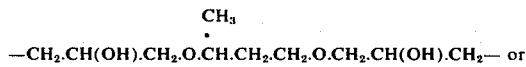

—$CH_2.CH(OH).CH_2.O.CH_2.CH_2.O.CH_2.CH_2.O.CH_2.CH(OH).CH_2$— or

—$CH_2.CH(OH).CH_2.O.CH_2.CH(OH).CH_2.O.CH_2.CH(OH).CH_2$— or

—$CH_2.CH(OH).CH(OH).CH_2$— or

—$CH_2.CH(OH).CH_2.O.CH_2.CH(OH).CH_2.O.(CH_2)_2.O.CH_2.CH(OH).CH_2.O.CH_2.CH(OH).CH_2$— or

—$CH_2.CH(OH).CH_2.O.CH_2.CH(OH).CH_2.O.(CH_2)_4.O.CH_2.CH(OH.CH_2.O.CH_2.CH(OH.CH_2$— or

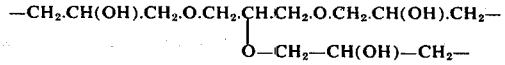

According to the invention, the polymerization products containing amino groups are in granular form, thereby facilitating their oral administration. The granular form of the polymerization product according to the invention can be obtained either by producing the polymer in the form of large lumps, e.g. blocks and disintegrating the lumps, e.g. by grinding, or by producing the product directly in the form of spherical granules, in accordance with pearl polymer techniques (dispersion polymerization). When applied orally graules obtained by reducing lumps by grinding may leave a gritty sensation in the mouth, and consequently, in order to avoid this unpleasantness, it can be to advantage to produce the products directly in the form of spherical granules. From the aspect of use, it is also to advantage if the major portion of the granular product has a particle size lying between 1 and 1000 μ, preferably between 10 and 800 μ, particularly between 20 and 600 μ, e.g. between 30 and 400 μ, such as between 50 and 300 μ. By particle size is meant here in the examples and claims the size of the particles when they are in a water-swollen state.

One important factor in respect of the therapeutical utility of the polymerization product is its ion-exchange capacity. One measurement of this is the ion-exchange capacity of chloride ions. The ion exchange capacity of the new compounds may, as before mentioned, vary between 0.2 and 1 milliequivalent chloride ion per 100 mg dry gel, the values between 0.3 and 0.9 being preferred. The novel products also possess good ion exchange properties with respect to organic acids of high molecular weight, such as bile acids and conjugated bile acids for example. If the polymerization products are to be used to bind acids of the aforementioned type, good results are obtained with products having good swelling ability, since the binding ability of, e.g., the bile acids will then be of the same magnitude as the ion-exchange capacity of chloride ions.

The invention also relates to a method for producing the polymerization products containing amino groups. The method is characterized in that a solution of the diamine of formula I above containing at least 2 g/100 ml of reaction volume, preferably at least 5 g/100 ml reaction volume, is reacted with one or more at least bifunctional substances of the formula $X.R_1.Z$ (II) or $$X.R_2.Z \quad \text{(III)},$$
$$\overset{Y}{\phantom{X.R_2.Z}}$$

where X, Y and Z are each a halogen atom, preferably chlorine or bromine and $R_1$ and $R_2$ are each a straight or branched aliphatic, saturated hydrocarbon chain substituted with one or more hydroxyl groups and containing 3–30 carbon atoms, preferably 3–16 carbon atoms and which is optionally broken by one or more oxygen atoms or with corresponding epoxy compounds capable of being obtained from the compounds (II) or (III) by splitting off hydrogen halide, to form an insoluble product, the quantity of the bifunctional substance or substances being adapted to the quantity of diamine and the reaction volume to provide a product having the desired degree of swellability in water and ion exchange capacity, whereafter the product, if necessary, is disintegrated to the desired particle size, and in that the product is optionally converted to a non-toxic salt. The product is recovered either with the amino groups in free form or in salt form. Examples of the product with amino groups in salt form include such where the amino groups are completely or partially converted to hydrochloride form.

A bifunctional cross-linking agent is preferably selected, the bifunctional cross-linking agent (II) or corresponding epoxy compound capable of being obtained from the compound (II) by splitting off the hydrogen halide is reacted with the diamine of the formula (I) in a molar relationship between the compound (II) or the epoxy compound and the diamine of the formula (1) greater than 1. The content of diamine in the solution may vary within wide limits. It should not, however, exceed approximately 90 gr/100 ml reaction volume. As before mentioned, the content of diamine shall be at least 2 gr per 100 ml reaction volume, preferably at least 5 gr/100 ml reaction volume. A particularly satisfactory result can be obtained if the diamine is present in the solution in a quantity of 10–80 gr/100 ml reaction volume, e.g. 20–70 gr/100 ml reaction volume.

The molar relationship between the compound of the formula $X.R_1.Z$ or $$X.R_2.Z \atop \overset{Y}{\phantom{X}}$$

or corresponding epoxy compound and the diamine with the formula (I) may also vary between wide limits. Values higher than approximately 5 on the ratio are not suitably used however. The ratio should preferably not exceed approximately 3.

As an example of the bifunctional substances of the formula $X.R_1.Z$ and corresponding epoxy compounds obtainable from $X.R_1.Z$ by splitting off the hydrogen halide can be mentioned:

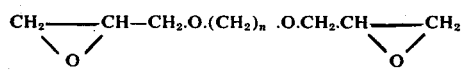

where $n_1$ is an integer from 2 to 4, and

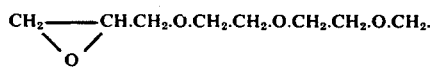

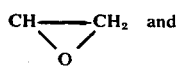

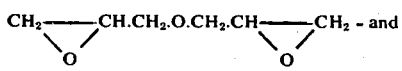

and

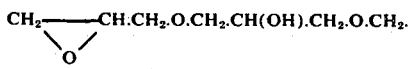

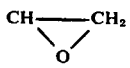

or corresponding halogen hydrins, and bifunctional glycerol derivatives of the formula $X . CH_2 . CH(OH) . CH_2 — Z$, e.g. dichlorohydrin and dibromohydrin or corresponding epoxy compounds obtainable by splitting off hydrogen halide and having the formula

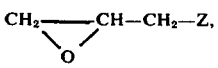

e.g. epichlorohydrin and epibromohydrin. Another example of such a bifunctional compound is 1,2 - 3,4-diepoxy-butan of the formula

Example of trifunctional bridge builders comprising epoxy compounds corresponding to the compounds of the formula $$\begin{array}{c} Y \\ X.R_2.Z \end{array}$$

is

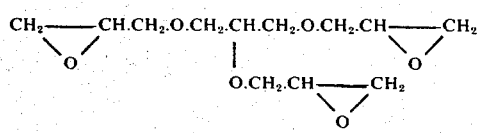

The reaction is carried out in the presence of a solvent in such quantities that the obtained product obtains the prescribed degree of swellability in water. It can thus be affected in an aqueous solution or a solution of an aqueous liquid. It is also possible, however, to use other solvents in which the diamine dissolves to intended concentrations, e.g. acetone or other lower aliphatic ketones, ethers etc. The reaction is catalysed by alkaline reacting substances such as alkalimetal hydroxides. The alkaline substance may also act as an acceptor for hydrogen halide, if such is liberated during the reaction. The alkaline reacting substance may also comprise the diamine (I) itself. The reaction is suitably effected at temperatures below 100°C, e.g. within the temperature range of 0°–80°C. If it is desired to avoid a rapid reaction, the reaction mixture may be chilled and/or the cross linking agent added slowly.

In accordance with the invention, the reaction can be effected as a block polymerization process, whereafter the obtained gel products are crushed to the desired particle size.

The solution of diamine may also be dispersed to droplet form in a solvent immiscible with the diamine. This method is applied if it is desired to produce the product directly in particle form (dispersion polymerization). If the reaction is carried out as a dispersion polymerization process, a solution of the diamine can be mixed with a liquid capable of forming a two-phase system therewith, while agitating the mixture under such conditions that the solution is converted to droplet form, whereupon the bridge builder, i.e. the substance of the formula $X.R_1.Z$ or $$\begin{array}{c} Y \\ X.R_2.Z \end{array}$$

or corresponding epoxy compound according to the aforegoing is caused to react with the diamine until a gel is obtained, whereupon the gel grains formed from the droplets can be recovered. The continuous phase in the two-phase system may comprise liquids which are immiscible with the solvent for the diamine. Suitable liquids in this context are aliphatic and aromatic hydrocarbons, halogenated aliphatic and aromatic hydrocarbons such as dichloromethane, 1,2-dichloroethane and 1,2-dibromomethane, o-dichlorobenzene etc. Dispersion polymerization also has the added advantage that the exothermic reaction is more easily controlled. The reaction is carried out suitably in an alkaline environment, which can be obtained by the presence of the diamine. Other alkaline reacting substances such as alkalimetal hydroxides, e.g. sodium hydroxide may also be added to the system.

For the purpose of stabilizing the dispersion of the diamine solution, it is suitable in accordance with the invention to add a stabilizer, e.g. a fatty acid. Preferably higher fatty acids such as stearic acid in free form or in salt form are used. Other stabilizers include water-insoluble polymers such as polyvinylacetate, polystyrene, polyisobutylene and cellulose acetatebutyrate. It has been discovered that the average molecular weight of the polymers plays an important part in respect of their stabilzing effect, since products having higher average molecular weights show a superior stabilizing effect on the dispersion than products having lower average molecular weight under otherwise similar conditions. The quantity of stabilizer is suitably referred to the quantity of the liquid comprising the continuous phase. Suitable quantities of stabilizer are 0.1 – 15 %, calculated in weight/volume.

The stabilizer can be removed from the formed gel grains by treating with a suitable solvent. When using high molecular stabilizers which can be hydrolyzed under relatively mild conditions, it may be convenient to first treat the gel grain with a hydrolyzing substance, such as alkalihydroxide, and then remove the hydrolyzed product by means of a solvent. High molecular esters, such as polyvinylacetate and cellulose acetatebutyrate, can be treated with a low percent alkalihydroxide solution for hydrolysis of the esters, whereupon the formed high molecular alcohols are removed by washing with a suitable solvent.

Under certain condtions it may be suitable to add a relatively low molecular surface active substance to the reaction mixture. If water-insoluble high polymer stabilizers are used, for example an exceedingly high percentage of polystyrene in combination with acetylbutyryl cellulose is added, a gel is obtained whose three-dimensional network will accomodate larger molecules than the three-dimensional network for the products obtained with higher fatty acids as stabilizers. This is an advantage for binding large molecules or aggregates of such molecules, for example salts of bile acids and conjugated bile acids. The maximum limit for the molecular size capable of penetrating into the gel grains (exclusion limit) is established for the demands in accordance with the invention by packing the gel in chromatography columns. Different dextran fractions with increasing average molecular weights are gel filtered in these columns. The elution volume, $V_e$, for each fraction is determined by refractometric detection. The void volume, $V_o$, is determined with a fraction of native dextran having an average molecular weight of $> 50 \cdot 10^6$. The total volume, $V_t$, of the column is calculated from its diameter and height. With the data thus obtained, a $K_{av}$-value for each gel filered dextran fraction can be determined. $K_{av}$ is the distribution or parting coefficient with separation between liquid and gel phase. The following expression is used for calculating $K_{av}$:

$$K_{av} = \frac{V_e - V_o}{V_t - V_o}$$

The obtained $K_{av}$-values and their corresponding molecular weights are plotted in a diagram from which the exclusion limit can be established by extrapolation of the steep portion of the curve. The exclusion limit may lie between molecular weight approximately 600 and approximately 100.000, preferably between approximately 600 and approximately 25.000, the values between approximately 600 and approximately 14.000 being mentioned by way of example, e.g. between 1.000 and 10.000.

The agitation conditions are of particular importance during the first stage of the dispersion polymerization process, since the agitation process together with the stabilizer determines the magnitude of the droplets in the dispersed phase. In this connection it is possible for one of normal skill in the art to establish the most suitable agitation speed with respect to the desired gel particle size, by taking samples at different agitation speeds.

It is sometimes suitable to add the bifunctional bridge building substance when a suitable drop size has been obtained, whereby the reaction is initiated. The reaction continues until the bridge building substance has been consumed, or until the reaction is interrupted in some other way. Once a gel begins to form, the agitation process is of smaller importance to the particle size.

The novel polymerization products containing amino groups are advantageous, among other things, because a larger portion of their ion-exchange capacity can be utilized to bind bile acids. This can be shown by ion-exchanging tests in vitro, wherein the polymerization products are shaken with a solution of a salt of a bile acid and the concentration of said salt measured before and after shaking. For the purpose of utilizing this effect in vivo, the polymerization products are administered orally. If the ion-exchanger is applied partially saturated with chloride ions, free amino groups in the ion-exchanger are prevented from being used excessively to bind hydrochloric acid in the stomach.

It has been discovered with in vivo tests that high cholesterol values can be greatly reduced by oral administration of products produced in accordance with the invention. Thus, an xylylene-diamine copolymer (a mixture of meta- and para-xylenediamine in the ratio of 7:3) and epichlorohydrin having a swelling factor of 15 and a particle size of 100 - 1000 $\mu m$ when administered to hens which had obtained a high blood cholesterol value as a result of cholesterol rich diet, was shown to reduce the cholesterol values to normal values.

The invention therefore also relates to an orally administered pharmaceutical preparation showing blood cholesterol reducing effect and comprising or containing a water-insoluble polymerization product containing amino groups in granular form, which preparation is characterized in that the water-insoluble polymerization product containing amino groups comprises a product which a. is formed of residues of one or more diamines of the formula H$_2$N.CH$_2$.phenylene, CH$_2$.NH$_2$     (I)

which residues are held together by bridges between the residues to form a three-dimensional network, the bridges being bound to nitrogen atoms in the residues (I) and comprising straight or branched aliphatic saturated hydrocarbon chains substituted with one or more hydroxyl groups and containing 3–30 carbon atoms, preferably 3–16 carbon atoms, and which are optionally broken by one or more oxygen atoms, the amino groups being present in either a free form or in the form of (the cation portion of) a non-toxic salt, and b. in insoluble in water or other solvents but swellable in water to a gel, 1 gr of the dry product in the form of HCl-salt in the presence of the water swelling to at least 5 ml and to at most 50 ml, preferably to at least 5 ml and to at most 25 ml, and c. comprises grains having a particle size substantially within the range 1 to 1000 $\mu$, preferably 10 to 800 $\mu$, and d. has an ion-exchanger capacity within the range 0.2 to 1 milliequivalent chloride ions, preferably 0.3 to 0.9 milliequivalent chloride ion, per 100 milligram dry gel.

The polymerization products can be administered orally, either as such, optionally suspended in liquids, or in the form of granulates, tablets or capsules. For the purpose of forming the polymerization products into dosage units, they can be mixed with physiologically acceptable carriers and the resultant mixture pressed or shaped in some appropriate manner. Examples of physiologically acceptable carriers for the dosage units include, for example, starch, tragacanth or magnesium stearte. Water, fruit juices etc. can be used as the suspension vehicle. The products may also be admixed with conventional foodstuffs.

The polymerization product containing amino groups is present in the composition according to the invention in the form of pearls obtained by pearl polymerization (dispersion polymerization) or as grains obtained by disintegration of the product when obtained by block polymerization. The polymerization product containing amino groups also suitably presents cavities in its network, these cavities being of such magnitude that bile acids and salts thereof are able to penetrate therein when the polymerization product exists in a water-swollen state.

A suitable dosage is 0.5 – 30 gr polymerization product per day for human beings, preferably 2–20 gr, especially 3–15 gr. The dosage can be divided into parts doses to be taken at intervals during the day, e.g. 3 × 4 gr or 3 × 3 gr or 3 × 5 gr per day. Each dosage unit may contain for example 0.5–5 gr.

Other substances showing therapeutical or other properties may be incorporated in preparations containing polymerization products produced in accordance with the invention.

The products according to the invention present when administered orally an advantageous combination of the properties desirable with respect to therapeutical effect and therapeutical acceptability.

The invention will now be illustrated with reference to a number of Examples.

EXAMPLE 1

Gel in pearl form of xylylene diamine and epichlorohydrin 1.25 gr of stearic acid was dissolved in 200 ml n-hexane. 25 gr of fine grained calcium carbonate, covered on the surface with 3 % of calcium stearate, were added. The mixture was stirred to obtain a homogeneous suspension. 52 ml of a mixture comprising meta- and para-xylylenediamine in the relationship 7:3, 1 gr calcium chloride and 30 gr water were then added. The mixture was stirred with an anchor agitator at a speed of 200 rpm and heated to 60°C. After 30 minutes, 64 gr of epichlorohydrin were added dropwise over a period of 30 minutes. The reaction was allowed to proceed for 5 hours, whereafter water and 12 N hydrochloric acid were added to obtain a pH of 1. The product was washed by repeated slurring in water until a pH of 5 was obtained. The product was shrunk on filters with ethanol, sucked off and dried in a vacuum drier at 50°C for 48 hours. Yield: 110 gr of white pearls. Particle size approximately 600μ. Analysis: N 8.3 %, moisture 28.8 %, Cl 29.8 %. 1 gr dry substance swelled to a volume of 15 ml in water. Ion-exchange capacity: 100 mg of dry substance binds 0.70 milliequivalents chloride ions. When administered to hens in cholesterol-enriched food, which gives an elevated cholesterol content in serum, the increase was reduced by > 100 %.

EXAMPLE 2

Gel of xylylene-diamine and epichlorohydrin 26 ml of a mixture comprising meta- and para-xylylene-diamine in the ratio 7:3 and 20 ml of water were mixed in a reaction vessel provided with an agitator. At 0°C, 24 ml epichlorohydrin were slowly added dropwise for 5 hours under agitation. After 24 hours 20 ml of water and 1 ml of tetraethylene-pentamine were added (to facilitate gel formation), whereafter a further 2 ml of epichlorohydrin were added dropwise.

The reaction mixture was then left to stand at 20°C for four days. The resulting gel was cut into pieces and washed with water. The water-containing gel lumps were then crushed to an average particle size of approximately 100μ. The gel particles were then washed, first with 0.1 N hydrochloric acid and then copiously with water. The product was then dried in a vacuum drier at 50°C for several days. 1 gr dry substance swells to a volume of 9 ml in water.

EXAMPLE 3

Gel in pearl form of m-xylylene-diamine and epichlorohydrin 3.1 gr of stearic acid were dissolved in 500 ml n-hexane. 62 gr fine-grained calcium carbonate, covered on the surface with 3 % calcium stearate, were added. The mixture was stirred until it was homogeneous. 136 gr of m-xylylene-diamine, 2.5 gr of calcium chloride and 75 gr of water were then added. The mixture was stirred with an anchor agitator at a speed of 300 rpm and heated to 50°C. After 30 minutes 92.5 gr of epichlorohydrin were added dropwise over a period of 30 minutes. The reaction was allowed to continue for 16 hours, whereafter water and 12 N hydrochloric acid were added to obtain a pH 1. The product was washed by repeated slurring in water until a ph of 5 was obtained. The product was shrunk on filters with 96 % ethanol, sucked off and dried in a vcuum drier at 50°C for 48 hours. Yield: 140 gr light-yellow pearls. Particle size: 100 – 150 μ. Analysis: N 9.7 %, Cl 20.5 %, moisture 7.8 %. 1 gr dry substance swells to a volume of 14.5 ml in water. The ion-exchange capacity: 100 mg of dry substance binds 0.617 meq. chloride ions. Administration to hens in cholesterol-enriched food, which causes an elevated cholesterol content in serum, reduces the increase by 62 %.

EXAMPLE 4

Gel of xylylene diamine and 1:3-glycerol diglycideether 1.5 gr of stearic acid were dissolved in 300 ml n-hexane. 31 gr of fine-grained calcium carbonate, covered on the surface with 3 % calcium stearate, were added. The mixture was stirred until homogeneous. 68 gr of a mixture comprising meta- and para-xylylene diamine in the ratio 7:3, 1.25 gr of calcium chloride and 37 gr of water were then added. The mixture was stirred with an anchor agitator at a speed of 250 rpm and heated to 40°C. After 30 minutes, 173 gr of 1.3 glycerol diglycide ether were added over a period of 30 minutes. The reaction was allowed to continue for 18 hours, after which water and 12 N hydrochloric acid were added to obtain a pH 1. The product was washed by repeated slurrying in water until a pH of 5 was obtained. The product was shrunk on filters with 96 % ethanol, sucked off and dried in a vacuum drier at 50°C for 48 hours. Yield: 175 gr light-yellow gel grains. particle size approximately 300 μ. Analysis: 4.7 %, moisture 6.4 %, Cl 18.9%. 1 gr dry substance swells to a volume of 10 ml of water. Ion-exchange capacity: 100 mg dry substance binds 0.30 milliequivalents chloride ions. Administration to hens in cholesterol enriched food, which causes elevated cholesterol content in serum, reduces the increase by 59 %.

EXAMPLE 5

Gel of xylylene diamine and epichlorohydrin 136 gr of a mixture comprising meta- and para-xylylene diamine in the ratio 7:3, 75 ml of water and 3 gr of sodium hydroxide were mixed in a reaction vessel equipped with an agitator. With the temperature of the mixture at 45°C, 92.5 gr epichlorohydrin were added dropwise over a period of 40 minutes. The reaction was allowed to cotinue for 24 hours. The temperature was then increased to 70°C and the reaction allowed to cotinue for a further 3 hours. After 24 hours at room temperature, water was added and the mixture was acidified to pH 1 with 12 N hydrochloric acid and stirred for 24 hours. The product was washed with water and shrunk with 96 % ethanol. The product was then swollen again in water and washed with water until a pH of 5 was obtained. The product was then crushed into small particles, shrunk with 96 % ethanol and dried in vacuum at 50°C for 48 hours. Yield: 190.5 gr of light-yellow substance. Analysis: N 9.3 %, Cl 19.8 %, moisture 13.7 %. 1 gr of dry substance swells to volume of 18 ml. Ion-exchange capacity: 100 mg of dry substance binds 0.62 milliequivalents chloride ions. Administration to hens in cholesterol-enriched food, which causes an elevated cholesterol content in serum, reduces the increase by 61 %.

EXAMPLE 6

Gel in pearl form of xylylene diamine and epichlorohydrin 1.25 gr of stearic acid were dissolved in 200 ml n-heptane. 25 gr fine-grained calcium carbonate, covered on the surface with 3 % calcium stearate, were added. The mixture was stirred to obtain a homogeneous suspension. 58.5 gr of a mixture comprising meta- and para-xylylene diamine in the ratio 7:3, 1 gr of calcium chloride and 30 gr of water were then added. The mixture was stirred with an anchor agitator at a speed of 250 rpm and heated to 50°C. After 30 minutes, 62.5 gr of epichlorohydrin were added dropwise over a period of 30 minutes. The reaction was allowed to continue for 16 hours, whereafter water and 12 N hydrochloric acid were added to obtain pH 1. The product was washed by repeated slurrying in water until a pH of 5 was obtained. The product was shrunk on filters with 96 % ethanol, sucked off and dried in a vacuum drier at 50°C for 48 hours. Yield: 94 gr of pale yellow pearls. Particle size 100–700 μ. Analysis: N 9.1 %, Cl 21.4 %, moisture 2.5 %. 1 gr dry substance swells to a volume of 5.8 ml in water. Ion-exchange capacity: 100 mg of dry substance binds 0.50 milliequivalents chloride ions.

EXAMPLE 7

Gel in pearl form of xylylene diamine and epichlorohydrin 0.6 gr of stearic acid was dissolved in 185 ml of n-hexane. 12 gr of fine-grained calcium carbonate, covered on the surface with 3 % calcium stearate, were added. The mixture was stirred to obtain a homogeneous suspension. 13 gr of a mixture of meta and para-xylylene diamine in the ratio 7:3 and 50 ml 1 N sodium hydroxide solution were then added. The mixture as stirred with an anchor agitator at a speed of 250 rpm and heated to 45°C. After 30 minutes, 9.5 gr of epichlorohydrin were added dropwise over a period of 30 minutes. The reaction was allowed to continue for 16 hours, whereafter water and 12 N hydrochloric acid were added to obtain pH 1. The product was washed by repeated slurrying in water until a pH of 5 was obtained. The product was then shrunk on filters with ethanol, sucked off and dried in vacuum at 50°C for 48 hours. Yield: 17 gr of white pearls. Particle size approximately 1000 $\mu$. Analysis: N 9.0%, cl 18.5 %, moisture 14.8 %. 1 gr dry substance swells to a volume of 10 ml in water. Ion-exchange capacity: 100 mg dry substance binds 0.62 milliequivlents chloride ions.

EXAMPLE 8

Polymerization product produced in accordance with the method described in Example 1 was dispensed in unit bags, each bag containing 4 gr of the granular polymerization product having a particle size of approximately 600 $\mu$, or corresponding product group to a particle size of approximately 100 $\mu$, whereafter the bags were closed.

The content of one bag is intended as a dosage unit for one fully grown person. The dosage of 4 gr is intended to be taken three times a day. When taken orally, the content of the bag is suitably stirred into a glass of water, fruit juice or other potable liquid, whereafter the suspension is swallowed. The dosage is intended to be repeated daily for patients with high blood cholesterol values until the desired reduction in the cholesterol values is obtained.

In the same way, dosage units containing 3 and 5 gr of the polymerization product per bag were prepared. These are intended to be used in such cases where a slightly lower or a slightly higher dosage is desired.

EXAMPLE 9

Polymerization product produced in accordance with the method described in Example 5 having an average particle size of approximately 100 $\mu$ were well mixed with sodium alginate in fine-grained powder form (approximately 100$\mu$ in dry form), the weight relationship between the polymerization product and the sodium alginate being 4:1. (Small quantities of different flavouring agents, e.g. one part by weight orange essence per 1000 parts by weight mixture may also be added to the mixture). The mixture was dispensed into unit bags, each bag containing 5 gr of the mixture, whereafter the bags were sealed.

The content of a bag represents the dosage for a fully grown person. The dosage of 5 gr mixture is intended to be taken 3 times a day. When taken orally, the content of the bag is suitably stirred into a glass of water, fruit juice or other potable liquid, whereafter the suspension is swallowed. The dosage is intended to be repeated daily for patients with high blood cholesterol vlues, until the desired reduction in the cholesterol values is obtained.

In the same way, dosage bags containing 4 gr and 6 gr of the mixture per bag were prepared. These are intended to be used when a slightly lower or a slightly higher dosage is desired.

We claim:

1. A pharmaceutical product for oral administration to mammals and birds having an elevated serum cholesterol level in their blood, which product contains a physiologically acceptable carrier and a cholesterol lowering amount of a water-insoluble polymer containing amino groups and which polymer
   a. contains residues of at least one diamine of the general formula $$H_2N.CH_2.phenylene.CH_2.NH_2 \qquad (I)$$

which residues are interconnected by bridges between the residues to form a three-dimensional network, the bridges being bound to nitrogen atoms in the residues (I) and comprise straight or branched aliphatic, saturated hydrocarbon chains substituted with one to four hydroxyl groups and containing 3 – 16 carbon atoms and which are unbroken or broken by one to four oxygen atoms, the amino groups being present in a free form or in the form of the cation portion of a non-toxic salt, and
   b. is insoluble in water, but capable of swelling in water to a gel, 1 g of the dry polymer in the form of the hydrochloride in the presence of water swelling to a volume within the range of 5 to 50 ml, inclusive, and
   c. is in grain form having a particle size within the range of 1 to 1000 $\mu$, and
   d. has an ion-exchange capacity within the range of 0.2 to 1 milliequivalent chloride ions per 100 mg of dry gel.

2. A product according to claim 1 which contains 0.5 – 30 gms of said polymer.

3. A pharmaceutical product according to claim 1, wherein the polymer containing amino groups is in the form of spherical granules.

4. A pharmaceutical product according to claim 1, wherein the three-dimensional network of the polymer allows bile acids and salts thereof to penetrate thereinto when the product is in a water swollen state.

5. A pharmaceutical product according to claim 1, wherein 1 g of the dry polymer in the form of the hydrochloride in the presence of water swells to at least 5 ml and to at most 25 ml.

6. A pharmaceutical product according to claim 1, wherein the polymer is in grain form having a particle size within the range of 10 to 800 $\mu$.

7. A pharmaceutical product according to claim 1, wherein the polymer has an ion-exchange capacity within the range of 0.3 to 0.9 milliequivalent chloride ions per 100 mg of dry gel.

8. A pharmaceutical product for oral administration to mammals and birds having an elevated serum cholesterol level in their blood, which product contains a physiologically acceptable carrier and a cholesterol lowering amount of a waterinsoluble polymer containing amino groups and which polymer a. contains residues of one or more diamines of the formula $$H_2H.CH_2.phenylene.CH_2.NH_2 \qquad (I)$$

which residues are held together by bridges between the residues to form a three-dimensional network, the bridges being bound to nitrogen atoms in the residues (I) and comprising straight or branched aliphatic saturated hydrocarbon chains substituted with one to four hydroxyl groups and containing 3 – 16 carbon atoms, and which are unbroken or broken by one to four oxygen atoms, the amino groups being present in a free form or in the form of the cation portion of a non-toxic salt, and b. is insoluble in water but swellable in water to a gel, 1 g of the dry polymer in the form of the hydrochloride in the presence of the water swelling to a volume within the range of from 5 to 50 ml, inclusive, and c. is in grain form having a particle size within the range of 10 to 800 $\mu$, and d. has an ion-exchange capacity within the range of 0.3 to 0.9 milliequivalent chloride ions per 100 mg of dry gel.

9. A product according to claim 8 which contains 0.5 – 30 g of said polymer.

10. A method of lowering the cholesterol content of the blood of mammals and birds having an elevated serum cholesterol level, said method consisting essentially of the oral administration of a physiologically acceptable carrier and a cholesterol lower amount of a polymer containing amino groups and which polymer a. is formed of residues of one or more diamines of the formula $$H_2N.CH_2.phenylene.CH_2.NH_2$$

which residues are held together by bridges between the residues to form a three-dimensional network, the bridges being bound to nitrogen atoms in the residues (I) and comprising straight or branched aliphatic saturated hydrocarbon chains substituted with one to four hydroxyl groups and containing 3 – 16 carbon atoms, and which are unbroken or broken by one to four oxygen atoms, the amino groups being present in either a free form or in the form of the cation portion of a non-toxic salt, and b. is insoluble in water but swellable in water to a gel, 1 g of the dry polymer in the form of the hydrochloride in the presence of the water swelling to a volume within the range of from 5 to 50 ml, inclusive, and c. comprises grains having a particle size within the range of 1 to 1000 $\mu$, and d. has a ion-exchange capacity within the range of 0.2 to 1 milliequivalent chloride ions per 100 my of dry gel.

11. A method according to claim 10 wherein said polymer is administered in an amount of 0.5 to 30 g per day.

12. A method according to claim 10 wherein said polymer is administered in an amount of 3 to 15 g per day.

13. A method of lowering the cholesterol content of the blood of mammals and birds having an elevated serum cholesterol level said method consisting essentially of the oral administration of a physiologically active carrier and a cholesterol lowering amount of a polymer containing amino groups and which polymer a. is formed of residues of one or more diamines of the formula $$H_2N.CH_2.phenylene.CH_2NH_2 \qquad (I)$$

which residues are held together by bridges between the residues to form a three-dimensional network, the bridges being bound to nitrogen atoms in the residues (I) and comprising straight or branched aliphatic saturated hydrocarbon chains substituted with one to four hydroxyl groups and containing 3 – 16 carbon atoms, and which are unbroken or broken by 1 to 4 oxygen atoms, the amino groups being present in either a free form or in the form of the cation portion of a non-toxic salt, and b. is insoluble in water but swellable in water to a gel, 1 g of the dry polymer in the form of the hydrochloride in the presence of the water swelling to a volume within the range of from 5 to 50 ml, inclusive, and c. comprises grains having a particle size within the range of 10 to 800 $\mu$, and d. has an ion-exchange capacity within the range of 0.3 to 0.9 milliequivalent chloride ion per 100 mg of dry gel.

14. A method according to claim 13 wherein said polymer is administered in an amount of between 0.5 to 30 g per day.

* * * * *